US010189957B2

(12) United States Patent
Brzeczko et al.

(10) Patent No.: US 10,189,957 B2
(45) Date of Patent: Jan. 29, 2019

(54) FORMULATION PROCESS METHOD TO PRODUCE SPRAY DRIED PRODUCTS

(75) Inventors: Albert W. Brzeczko, Baltimore, MD (US); John A. Doney, Washington, DC (US)

(73) Assignee: ISP INVESTMENTS LLC, Wilmington, DE (US)

( * ) Notice: Subject to any disclaimer, the term of this patent is extended or adjusted under 35 U.S.C. 154(b) by 1107 days.

(21) Appl. No.: 12/019,889

(22) Filed: Jan. 25, 2008

(65) Prior Publication Data
US 2008/0181962 A1    Jul. 31, 2008

Related U.S. Application Data
(60) Provisional application No. 60/886,750, filed on Jan. 26, 2007.

(51) Int. Cl.
*A61K 9/14*      (2006.01)
*C08J 3/12*      (2006.01)
*A61K 9/16*      (2006.01)
*C08J 3/205*     (2006.01)

(52) U.S. Cl.
CPC ............. *C08J 3/122* (2013.01); *A61K 9/1635* (2013.01); *A61K 9/1694* (2013.01); *C08J 3/205* (2013.01)

(58) Field of Classification Search
None
See application file for complete search history.

(56) References Cited

U.S. PATENT DOCUMENTS

| | | | |
|---|---|---|---|
| 3,450,494 A | 6/1969 | Gaiser | |
| 3,981,676 A | 9/1976 | Ghilardi et al. | |
| 4,209,912 A | 7/1980 | Barker | |
| 4,572,915 A | 2/1986 | Crooks | |
| 4,826,689 A | 5/1989 | Violanto et al. | |
| 4,956,386 A | 9/1990 | McLoughlin et al. | |
| 5,012,975 A | 5/1991 | Korsmeyer | |
| 5,100,679 A | 3/1992 | Delrue | |
| 5,340,591 A | 8/1994 | Nakano et al. | |
| 5,443,842 A | 8/1995 | Seghizzi et al. | |
| 5,519,021 A | 5/1996 | Young et al. | |
| 5,663,169 A | 9/1997 | Young et al. | |
| 5,665,720 A | 9/1997 | Young et al. | |
| 5,770,559 A | 6/1998 | Manning et al. | |
| 5,811,423 A | 9/1998 | Young et al. | |
| 5,824,357 A | 10/1998 | Chaveron et al. | |
| 5,871,775 A | 2/1999 | Valducci | |
| 5,958,458 A | 9/1999 | Norling et al. | |
| 5,989,583 A | 11/1999 | Amselem | |
| 6,056,791 A | 5/2000 | Weidner et al. | |
| 6,056,971 A | 5/2000 | Goldman | |
| 6,143,211 A | 11/2000 | Mathiowitz et al. | |
| 6,184,255 B1 | 2/2001 | Mae et al. | |
| 6,197,349 B1 | 3/2001 | Westesen et al. | |
| 6,221,398 B1 | 4/2001 | Jakupovic et al. | |
| 6,235,224 B1 | 5/2001 | Mathiowitz et al. | |
| 6,253,463 B1 | 7/2001 | Hansen | |
| 6,262,034 B1 | 7/2001 | Mathiowitz et al. | |
| 6,300,377 B1 | 10/2001 | Chopra | |
| 6,403,116 B1 | 6/2002 | Anderson et al. | |
| 6,462,093 B1 | 10/2002 | Miyamoto et al. | |
| 6,503,927 B1 | 1/2003 | Ronsen et al. | |
| 6,548,555 B1 | 4/2003 | Curatolo et al. | |
| 6,555,133 B2 | 4/2003 | Makooi-Morehead et al. | |
| 6,579,521 B2 | 6/2003 | Sahner | |
| 6,582,729 B1 | 6/2003 | Eljamal et al. | |
| 6,689,755 B1 | 2/2004 | Gabel et al. | |
| 6,723,359 B2 | 4/2004 | Subramaniam et al. | |
| 6,740,338 B1 | 5/2004 | Chopra | |
| 6,746,635 B2 | 6/2004 | Mathiowitz et al. | |
| 6,761,909 B1 * | 7/2004 | Etter | 424/489 |
| 6,763,607 B2 | 7/2004 | Beyerinck et al. | |
| 6,769,200 B2 | 8/2004 | Raehse et al. | |
| 6,923,988 B2 | 8/2005 | Patel et al. | |
| 6,973,741 B2 | 12/2005 | Beyerinck et al. | |
| 2002/0006443 A1 | 1/2002 | Curatolo et al. | |
| 2002/0009494 A1 | 1/2002 | Curatolo et al. | |
| 2002/0045668 A1 | 4/2002 | Dang et al. | |
| 2003/0049321 A1 | 3/2003 | Begon et al. | |
| 2003/0091643 A1 | 5/2003 | Friesen et al. | |
| 2003/0104063 A1 | 6/2003 | Babcock et al. | |
| 2003/0147965 A1 | 8/2003 | Bassett et al. | |
| 2003/0157182 A1 | 8/2003 | Staniforth et al. | |
| 2003/0170309 A1 | 9/2003 | Babcock et al. | |
| 2003/0224043 A1 | 12/2003 | Appel et al. | |
| 2004/0013734 A1 | 1/2004 | Babcock et al. | |
| 2004/0138299 A1 * | 7/2004 | Cahill | A61K 31/277 514/521 |
| 2004/0175428 A1 * | 9/2004 | Appel | A61K 9/0004 424/473 |
| 2004/0194338 A1 | 10/2004 | Beyerinck et al. | |
| 2004/0220081 A1 | 11/2004 | Kreitz et al. | |

(Continued)

FOREIGN PATENT DOCUMENTS

| | | |
|---|---|---|
| EP | 1249232 | 10/2002 |
| GB | 988122 | 4/1965 |

(Continued)

OTHER PUBLICATIONS

Subramaniam, B., et al., "Pharmaceutical Processing with Supercritical Carbon Dioxide," Journal of Pharmaceutical Sciences 86(8): 885-890 (1997).*

(Continued)

*Primary Examiner* — David J Blanchard
*Assistant Examiner* — Daniel F. Coughlin
(74) *Attorney, Agent, or Firm* — Thompson Hine LLP; William J. Davis

(57) ABSTRACT

A method for preparing solid materials is described. One aspect of the method includes the steps of (a) providing a feedstock comprising an organic material(s) in a solvent system containing a non-solvent for the organic material at an elevated temperature and/or pressure above ambient conditions, (b) distributing the feedstock into either droplets or a film, and (d) evaporating the solvent system from the feedstock.

19 Claims, 7 Drawing Sheets

(56) References Cited

U.S. PATENT DOCUMENTS

| | | |
|---|---|---|
| 2005/0002870 A1 | 1/2005 | Osborne |
| 2005/0031692 A1 | 2/2005 | Beyerinck et al. |
| 2005/0049223 A1 | 3/2005 | Curatolo et al. |
| 2005/0079138 A1 | 4/2005 | Chickering, III et al. |
| 2005/0133949 A1 | 6/2005 | Stoy |
| 2005/0139144 A1 | 6/2005 | Muller et al. |
| 2005/0143404 A1 | 6/2005 | Rosenberg et al. |
| 2005/0169988 A1 | 8/2005 | Tao et al. |
| 2005/0170000 A1 | 8/2005 | Walker et al. |
| 2005/0170002 A1 | 8/2005 | Kipp et al. |
| 2006/0106230 A1 | 5/2006 | Pinchasov et al. |
| 2006/0216351 A1 | 9/2006 | Friesen et al. |
| 2008/0181962 A1 | 7/2008 | Brzeczko et al. |

FOREIGN PATENT DOCUMENTS

| | | |
|---|---|---|
| GB | 1138180 | 12/1968 |
| GB | 1201171 | 8/1970 |
| GB | 2401547 | 11/2004 |
| JP | 55-86501 | 6/1980 |
| WO | 97/13503 | 4/1997 |
| WO | 97/36577 | 10/1997 |
| WO | 00/40220 | 7/2000 |
| WO | 03/027170 | 4/2003 |
| WO | 03/043630 | 5/2003 |
| WO | 03/045327 | 6/2003 |
| WO | 03/049701 | 6/2003 |
| WO | 03/063821 | 8/2003 |
| WO | 03/068008 | 8/2003 |
| WO | 2004/098570 | 11/2004 |
| WO | 2005/000267 | 1/2005 |
| WO | 2005/041929 | 5/2005 |
| WO | 2005/055976 | 6/2005 |
| WO | 2006/082500 | 8/2006 |
| WO | 2006/134610 | 12/2006 |

OTHER PUBLICATIONS

"The Engineering Toolbox," at http://www.engineeringtoolbox.com/critical-point-d_997.html.*

Bain, D.F. et al., "Solvent Influence on Spray-Dried Biodegradable Microspheres," J. Microencapsulation, vol. 16, No. 4, pp. 453-474 (1999).

Buckton, G. et al., "The Effect of Spray-Drying Feed Temperature and Subsequent Crystallization Condition on the Physical Form of Lactose," *AAPS PharmSciTech*, 3(4) (6 pages) (2002).

Chew, N.Y.K. et al., "Use of Solid Corrugated Particles to Enhance Powder Aerosol Performance," Pharmaceutical Research, vol. 18, No. 11, pp. 1570-1577 (Nov. 2001).

Hancock, B.C. et al., "Molecular Mobility of Amorphous Pharmaceutical Solids Below Their Glass Transition Temperatures," Pharmaceutical Research, vol. 12, No. 6, pp. 799-806 (1995).

Kakumanu, V.K. et al., "Supercritical Fluid Technology in Pharmaceutical Research," *Business Briefing:Labtech*, p. 70-72 (2004).

Maa, Yuh-Fun et al., "The Effect of Operating and Formulation Variables on the Morphology of Spray-Dried Protein Particles," Pharmaceutical Development and Technology, 2(3), pp. 213-223 (1997).

Matsuda, Y. et al., "Improvement of the photostability of ubidecarenone microcapsules by incorporating fat-soluble vitamins," International Journal of Pharmaceutics 1985 Netherlands, vol. 26, No. 3, pp. 289-301 (1985).

PCT, International Preliminary Report on Patentability, PCT/US2006/029822 (dated Jan. 29, 2008).

PCT, International Preliminary Report on Patentability, PCT/US2006/029821 (dated Jan. 29, 2008).

PCT, International Preliminary Report on Patentability, PCT/US2006/029604 (dated Jan. 29, 2008).

PCT, International Search Report , PCT/US2006/029821 (dated Jun. 21, 2007).

PCT, International Search Report and Written Opinion, PCT/US2008/052003 (dated Jul. 16, 2008).

PCT, International Search Report, PCT/US2006/029604 (dated Feb. 14, 2008).

PCT, International Search Report, PCT/US2006/029822 (dated May 31, 2007).

Raula, J. et al., "Influence of the Solvent Composition on the Aerosol Synthesis of Pharmaceutical Polymer Nanoparticles," International Journal of Pharmaceutics, 284, pp. 13-21 (2004).

Sunkara, G. et al., "Drug Delivery Applications of Supercritical Fluid Technology," *Drug Delivery Technology*, Vo.. 2, No. 1 (8 pages) (Jan.-Feb. 2002)

Thybo, P., "Physical Stability of Spray Dried Solid Dispersions of Amorphous Tolfenamic Acid and Polyvinylpyrrolidone K-30," presented by The Danish University of Pharmaceutical Sciences, Copenhagen, Denmark (29 pages) (Oct. 2006).

"Training Papers Spray Drying," (English, Version B), published by BÜCHI Laboratecknik AG (19 pages) (Copyright 1997-2002).

XP0024247891 Database CA [Online] Chemical Abstracts Service, Columbus, Ohio, US "Pharmaceuticals containing ubidecarenone at high concentrations and effective dispersing agents" retrieved from STN.

Jirgensons, B. "Solubility and Fractionation of Polyvinylpyrrolidone," Journal of Polymer Science, 1952, vol. VII, No. 5, pp. 519-527.

Merriam-Webster's Collegiate Dictionary, 10th edition, Merriam-Webster, Inc.: Springfield, Massachusetts, 1996, pp. 48; (definition of "another").

* cited by examiner

FORMULATION PROCESS METHOD TO PRODUCE SPRAY DRIED PRODUCTS

CROSS REFERENCE TO RELATED APPLICATION

This application claims the benefit of U.S. Provisional Application Ser. No. 60/886,750, filed Jan. 26, 2007, the contents of which are hereby incorporated by reference.

BACKGROUND OF THE INVENTION

The present invention is directed to methods for producing spray dried products. More particularly, one aspect of the present invention relates to methods for preparing solid materials utilizing a feedstock comprising an organic material in a composition comprising a non-solvent for the organic material to produce a spray-dried composition wherein the feedstock is provided at an elevated temperature and/or elevated pressure relative to ambient conditions. In accordance with particular embodiments of the invention, the feedstock comprises a polymer and a pharmaceutically active material.

Spray drying is a particle processing technology that transforms a liquid feedstock into a powder product by first spraying the feedstock to create droplets, and then evaporating the feedstock liquid through the use of a heated drying medium, typically air. The liquid feedstock can take the form of a solution, suspension, liquid-paste, or emulsion, and must be pumpable and capable of droplet formation. Solutions are created when the feedstock liquid, termed a solvent, dissolves the product solids. Slurries and dispersions are created when the product solids do not dissolve in the feedstock liquid. The extensive application of spray drying to multiple industries, including agriculture, chemicals, dairy, and pharmaceuticals has resulted in the creation of technologies that aid in feedstock storage, pumping, atomization, drying, and product (powder) collection. An extensive review of the spray drying art is described by Masters (2002), which is incorporated herein by reference.

The competing heat and mass transfer processes central to the creation of spray dried powders significantly contribute to final product attributes. The evaporation of feedstock liquid and the simultaneous increase in droplet temperature (due to heat transfer supplied by the heated drying medium) create complex mechanisms of particle formation. Both feedstock formulation and spray dryer operation determine how solids form from the atomized feedstock droplet. A variety of final particle shapes, including smooth and ruptured spheres and irregular/fragmented forms, has been reported.

It can be difficult to produce dense, free-flowing spray dried powders when the feedstock comprises plastic film-forming materials (e.g., polymers). After atomization, the initial droplet surface is freely saturated with solvent, which readily evaporates in the drying medium. With subsequent solvent loss, a film may be produced, and for additional drying to occur, solvent must diffuse through this layer for evaporation to occur. Eventually, the film layer may sufficiently impede solvent diffusion/evaporation. This condition, known as case hardening, is undesirable for two reasons: First, it can be exceedingly difficult to remove additional solvent from case-hardened particles. Extensive secondary drying may be required to reduce the solvent content to acceptable levels. Second, the case-hardened particle may balloon in size as the trapped solvent is heated by the drying medium. Consequently, spray dried powders of film-forming materials may suffer from low bulk and tapped density in addition to unacceptably high residual solvent content. To resolve these limitations, those skilled in the art may have to rely on special nozzles or drying methods to limit temperature gradients that might otherwise induce case hardening and its negative consequences. Nonetheless, further drying steps may be needed to reduce this residual solvent content to levels acceptable for the finished product. Thus, there exists the need for methods to reduce case hardening in order to ease production and improve product quality.

An additional challenge to the production of spray dried powders is the atomization of discrete feedstock droplets. It is well known by those skilled in the art that viscous feedstocks may not atomize cleanly. Shear forces, necessary to break-up the feed into separate droplets, may be insufficient to overcome viscous forces at the point of atomization. As a result, the atomization device produces viscous threads, which can solidify in the drying medium. Such threads significantly reduce product quality due to their variable nature and poor flowability. The problem of high feedstock viscosity can be resolved by reducing solids concentration (which undesirably reduces production throughput), or by increasing feedstock temperature. The practice of heating the aqueous feedstocks, common in the milk and other foods industries, simultaneously helps to reduce microbial contamination. The effect of heated feedstock may increase or decrease powder density, depending on whether or not the increased feed temperature deaerates the feed [Masters, 2002].

Yet another disadvantage of conventional spray drying technology is the restriction imposed upon the feedstock formulation. It may be desired, for a variety of product quality and performance reasons, to incorporate preferred components in the feedstock to be spray dried. However, a lack of mutual solubilities in a common solvent may make it difficult or impossible to achieve. Other times, satisfactory solubility between feedstock components is achieved only through difficult-to-use or toxic solvents. For example, if the common solvent has an exceedingly high boiling point (e.g., dimethylsulfoxide, 189° C.), it can be difficult to remove the solvent through spray drying alone; the spray dried powder (if it can be produced) then requires extensive secondary drying. Alternatively, the common solvent may comprise an ICH Class I or II solvent (e.g., dichloromethane), whose toxicological and environmental concerns warrant special processing considerations. Thus, there exists the need for advanced spray drying processes to facilitate solubility and reduce or eliminate the need for difficult-to-use or toxic solvents.

Even when a feedstock formulation is achievable using conventional techniques, the performance of the spray dried powder may suffer from unacceptable properties, including: particle size, particle size distribution, bulk and/or tapped density, rate of active release, and/or extent of active release. Effective reformulation to resolve such properties may not be afforded using conventional techniques known to one skilled in the art. Thus, advanced methods are needed to increase formulation flexibility and create these desired compositions.

Contrary to this teaching, a utile process may not be provided for feedstocks comprising organic solvents when the drying chamber is maintained above the boiling point of the organic solvent—the nozzle may clog under these conditions. Accordingly, it may be advantageous to maintain the drying chamber at a temperature less than the boiling point of the solvent. Surprisingly, the condition of a heated drying medium may be unnecessary in order to produce a powder product; the drying chamber need not be appreciably heated above ambient conditions, and in fact the process gas may have to cool droplets of the high-energy feedstock.

SUMMARY OF THE INVENTION

The present invention relates to methods for producing powder and granulated products of enhanced attributes. In accordance with one aspect, the invention provides a method for producing powder or granulated products using a high-energy feedstock comprising an organic material in a composition containing a non-solvent for the organic material wherein the feedstock is maintained at elevated temperature, elevated pressure or both. A particularly useful embodiment pairs an active ingredient with one or more polymers that attain mutual solubility in the high-energy feedstock. Surprisingly, feedstock compositions can be produced that are otherwise impossible to create using conventional technologies.

Products produced in accordance with certain aspects of the present invention exhibit enhanced physical and chemical properties that improve process operation and product performance. Process advantages may include: a reduction or elimination of difficult-to-use and/or toxic solvents, and an enhanced production rate. Product performance advantages may include higher bulk and/or tapped density, narrower particle size distribution, better control of the particle size, faster rate of active release, higher extent of active release, and/or improved elimination of crystalline states of feedstock components.

DESCRIPTION OF THE INVENTION

Figure 1:
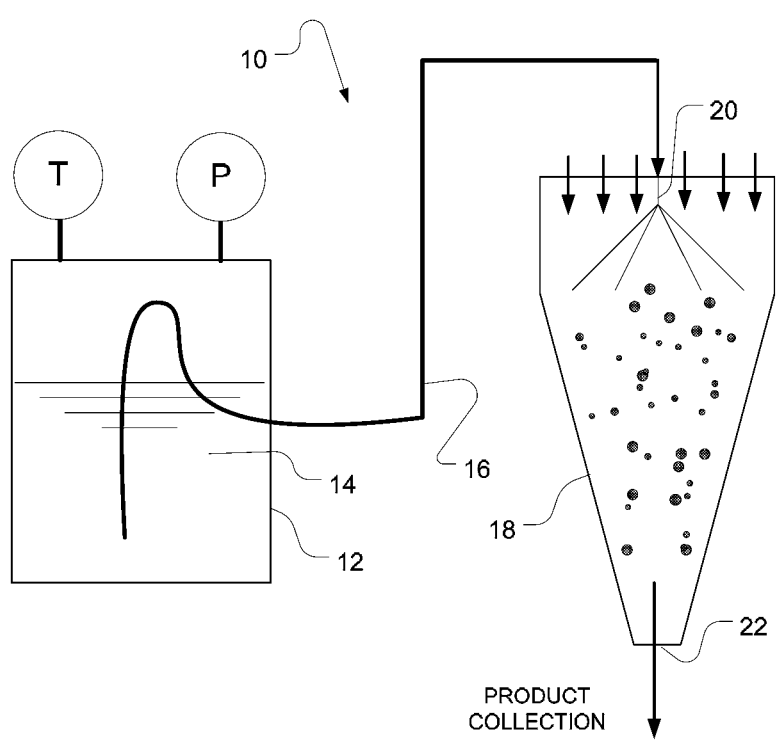
FIG. 1 is a schematic drawing of a spray dryer system in accordance with one aspect of the invention.

The term "comprising" encompasses the more restrictive terms "consisting essentially of" and "consisting of".

The phrase "ambient conditions" refers to the temperature and pressure typically prevalent in a room setting, about 20° C. and 1 atm.

All percentages, ratios and proportions used herein are by weight unless otherwise specified.

Bioavailability refers to the degree to which the active becomes available in the body after administration. Typically, plasma samples are taken and analyzed for the plasma concentration of the active. These data may be expressed as Cmax, the maximum amount of active ingredient found in the plasma, or as AUC, the area under the plasma concentration time curve. Enhanced bioavailability may be evidenced by an increase in Cmax and/or AUC for the active, the active metabolite or both. Compositions in accordance with certain aspects of the invention exhibit enhanced bioavailability compared to a control composition.

The term "solid dispersion" as used herein refers to a system in a solid state comprising at least two components, wherein one component is dispersed evenly throughout the other component or components. The term "solid dispersion" includes systems having small particles either completely crystalline, completely amorphous or any state in between, typically less than about 1 µm in diameter, of one phase dispersed in another phase.

The term "solid solution" as used herein refers to a type of solid dispersion wherein one component is molecularly dispersed throughout another component such that the system is chemically and physically uniform and homogeneous throughout. These systems do not contain any significant amounts of active ingredients in their crystalline or microcrystalline state as evidenced by thermal analysis or X-ray diffraction.

Spray drying is a well known process wherein a liquid feedstock is dispersed into droplets into a drying chamber along with a heated process gas stream to aid in solvent removal and produces a powder product. Heated aqueous feedstocks at standard pressure (i.e., at about 1 atm) have been used, especially in the dairy and soy industries, but only to the extent of reducing viscosity (to enable feedstock pumping and atomization into discrete droplets), increasing feedstock solids content (for economical production advantages), and to help control microbial contamination.

Spray dryer operation influences particle characteristics. Masters (1991) proposes that solvent evaporation from an atomized sphere progresses through three stages: Initially, when the droplet surface is saturated with solvent, evaporation proceeds at a constant rate and is called the first stage of drying. A change in the drying rate is noted with additional drying, due to the formation of dry solids on the surface. At this critical point the surface is no longer considered to be freely saturated with solvent. Further solvent evaporation from the droplet proceeds at a slower rate, requiring diffusion or capillary action through the solid surface layer. At this stage of drying, careful operation of the spray dryer is desirable to remove as much solvent as possible and to avoid expanding the droplet and producing a low density powder. Inlet and outlet temperatures must be controlled, as well as the flow configuration of the drying gas.

Nonetheless, it is sometimes impossible to avoid spray dryer operating conditions that can negatively impact product properties. Formulations containing film formers such as polymers in solvent(s) can quickly reach the critical point of surface evaporation, leading to a situation that approaches or reaches case hardening. Case hardening of the exterior polymer film can make complete or essentially complete solvent removal difficult or essentially impossible without damaging the spray dried powder. The solid polymer (or polymer-like) surface film can also lead to low density powders. Volumetric expansion of trapped solvent due to dryer operation produces low-density, thin-walled particles that are prone to rupture either during the drying step or material handling.

Spray dried powders produced in accordance with certain aspects of the present invention exhibit unusual properties due to particle morphologies created by the atomization of the high-energy feedstock. Such particle architecture and properties typically are not achievable through conventional spray drying methods at atmospheric pressure and with minimal temperature modification (i.e., feedstock temperature slightly elevated above 20° C.).

Yet, the selective customization of particle properties can offer intriguing opportunities for production processes and active delivery in a number of industries including pharmaceutical, healthcare, agricultural, personal care, biocide and industrial applications. The morphology of individual particles plays a central role in this pursuit, since morphology directly influences bulk powder properties, such as density, residual solvent content, and flowability. In addition, techniques that modify particle shape and interior structure may profoundly affect product properties, such as residual solvent content, active loading, crystallinity, release rate, solubility, and bioavailability. Thus, the ability to design particle morphology has significant implications for the production process and product attributes.

The present invention is directed toward a formulation process method for producing products of enhanced attributes preferably by, but not limited to, spray drying. More particularly, the present invention discloses methods and the products produced from preparing a feedstock comprising an organic material and a composition containing a non-solvent for the organic material. The described process involves using the feedstock at a temperature and/or pressure elevated above ambient conditions. At the elevated temperature and/or pressure, the non-solvent may function as a solvent for the organic material. The choice of organic material to be processed is not particularly restricted, and any number of compositions found in the pharmaceutical, healthcare, agricultural, personal care, biocide and industrial industries may be selected. Examples include biocides, dietary ingredients, dyes, nutritionals, pharmaceutical ingredients, polymers, salts, and blends thereof. In accordance with other embodiments, powders have been produced as small as 0.5 μm, a size suitable for inhalation delivery. Pharmaceutical spray dried powders in accordance with certain embodiments of the invention typically have a mean particle size of about 0.5 μm-500 μm. This organic material is then paired with a solvent system and maintained at an elevated temperature and/or pressure to create the formulation process method claimed by the claimed invention.

By selecting the appropriate organic material(s) and solvent(s)/non-solvent(s) and preparing a high energy feedstock as described herein, various improvements over conventional spray drying processes may be realized. More specifically, by practicing the present invention, it may be possible to:

1. Reduce or eliminate the need for difficult-to-use feedstock solvents;
2. Reduce or eliminate the need for toxic feedstock solvents;
3. Enhance the production rate;
4. Increase formulation flexibility;
5. Reduce residual solvent concentrations in the produced powders;
6. Improve control over the particle size;
7. Improve control over the particle size distribution;
8. Increase the rate of release of active ingredients;
9. Increase the extent of release of active ingredients;
10. Alter the solid state chemistry (reduce crystallinity of the organic material);
11. Create highly collapsed and/or dimpled particles; and/or
12. Enhance powder bulk and/or tapped density.

Another aspect of the invention relates to a spray drying process suitable for use with certain organic materials that have low solubility under conventional conditions. For example, active ingredients, such as pharmaceutical actives, exhibit a wide range of solubility in water and organic solvents. A ranking of solubility is provided in the United States Pharmacopeia (Table 1). It can be difficult to achieve economical spray dryer production rates for materials that are sparingly soluble (or less) in water or organic solvents. Additionally, formulations can be challenged when the organic material(s) has limited solubility. For other applications, high solubility is achieved only using solvents that present undesirable processing challenges, like high boiling point (e.g., dimethylsulfoxide) or toxicity (e.g., dichloromethane). In accordance with one aspect of the present invention, these problems may be resolved by heating and/or pressuring a feedstock comprising a more amenable feedstock solvent.

TABLE 1

Descriptive terms employed to describe solute solubility

| descriptive term | parts of solvent required for 1 part solute |
|---|---|
| very soluble | less than 1 |
| freely soluble | from 1 to 10 |
| soluble | from 10 to 30 |
| sparingly soluble | from 30 to 100 |
| slightly soluble | from 100 to 1,000 |
| very slightly soluble | from 1,000 to 10,000 |
| practically insoluble, or insoluble | more than 10,000 |

Although the following description is primarily directed to the preparation of a spray-dried composition, the present invention is not limited to spray-dried compositions. The scope of the present invention also includes methods for preparing other solid materials such as granules and other multiparticulate compositions. These solid materials may comprise any organic matter, such as a sugar, a polymer, an active substance, or mixtures of these materials. Those other solid materials can be prepared in accordance with conventional techniques such as high-shear granulation, fluid bed granulation, film coating or any of their related technologies.

In accordance with the present invention, a high-energy feedstock is provided wherein the feedstock is maintained at an elevated temperature and/or elevated pressure as compared to conventional spray dried operations wherein the feedstock is maintained at conventional ambient condition. The feedstock solution may be maintained at elevated temperature, elevated pressure or both elevated temperature and pressure. For example, for polyvinylpyrrolidone, a suitable solvent system is acetone and toluene at 150° C. and 10 psig, since this polymer does not dissolve in acetone/toluene blends under ambient conditions. The high-energy feedstock is then delivered to any device capable of atomizing the feedstock and presenting the spray into a chamber for particle formation. In one embodiment, traditional spray drying equipment is employed to produce the powder product.

A spray drying system in accordance with one aspect of the present invention is illustrated in FIG. 1. The spray-drying system (10) includes a closed feedstock supply tank (12) containing the feedstock (14). The feedstock (14) in the illustrated embodiment comprises a pharmaceutically active material and a polymer in a solvent/non-solvent blend. The feedstock (14) is maintained in the closed container at elevated temperature and/or elevated pressure. The feedstock solution (14) is fed through conduit (16) to a particle formation chamber (18). The conduit (16) is connected to an atomizer (20) located at the top of the chamber (18). The atomizer (20) may be of any conventional design (e.g., a rotary atomizer wheel, a pressurized nozzle, a two-fluid nozzle, etc.). The atomizer (20) distributes the feedstock solution (14) into fine droplets in the particle formation chamber (18), which may be provided with a process gas to facilitate solidification. The solvent evaporates from the droplets within the chamber (18) thereby forming solid dispersion particles of active material and polymer. The solid dispersion particles exit the chamber (18) out of an outlet (22) at the bottom of the chamber (18). The outlet (22) leaves to an apparatus for product collection.

In accordance with the present invention, a high energy feedstock is provided wherein the feedstock is maintained at an elevated temperature and/or elevated pressure as compared to conventional spray dried operations wherein the feedstock is maintained at conventional ambient conditions (i.e., 20° C. and 1 atm). In accordance with certain aspects of the present invention, the feedstock solution is maintained at temperatures and pressures above ambient but lower than the temperatures and pressures that decompose the organic material. More particularly, the feedstock temperature may be maintained at a temperature of from about ambient to about 200° C., more particularly from about 35° C. to about 115° C., and in accordance with certain embodiments from about 40° C. to about 80° C.

In accordance with other embodiments of the present invention, the feedstock solution is maintained at elevated pressures of greater than 1 atm. For example, the feedstock solution may be maintained in a closed container at pressures from about 0.1 to about 215 atm (gauge) more particularly from about 0.5 to about 20 atm (gauge) and in accordance with certain embodiments, from about 1 to about 10 atm (gauge). The feedstock solution may be maintained at elevated temperature, elevated pressure or both elevated temperature and pressure. The high energy feedstock is then delivered to traditional spray drying to atomize the feed, evaporate the solvent and produce the spray dried product.

While the feedstock may contain, without limitation, any organic material, the feedstock preferably comprises one or more polymers, and more preferably comprises an active ingredient with one or more polymers. In a preferred embodiment, the organic material comprises an active ingredient and/or solubility-enhancing organic material. When applied to manufacture products incorporating an active ingredient, a system of polymers can be used to modify not only particle morphology, but also the performance properties of the active.

One aspect of the invention involves the pairing of a polymer with a carefully selected solvent system. The organic material, which in one aspect of the invention is a polymer, may or may not be soluble in the solvent system at ambient conditions. The term "soluble" means that the attractive forces between polymer and solvent molecules are greater than the competing inter- and intramolecular attractive forces between polymer molecules and the polymer molecule expands. Guidance in defining polymer solubility is provided by the expansion coefficient ($\alpha$):

$$\alpha = \frac{(\bar{r}^2)^{1/2}}{(\bar{r}_o^2)^{1/2}} \tag{§1}$$

where $\bar{r}^2$ is the mean-square distance between chain ends, and $\bar{r}_o^2$ is the unperturbed dimension. (Equation § 1 can be written for branched polymers in an analogous manner, using square-average radius of gyration about the center of gravity, $\bar{s}^2$, and the corresponding unperturbed dimension, $\bar{s}_o^2$.) Polymer solubility is provided when $\alpha$ is unity or greater, and solvents that satisfy this condition are called "good solvents," or simply "solvents." Solvents uncoil (or expand) the polymer molecule, since the polymer-solvent attractive force is greater than that of polymer-polymer. Light scattering methods, (e.g., Triple Detector Array by Viscotek Corp.), can be used to determine the variables expressed in equation § 1. These concepts are defined in the text *Polymer Chemistry, An Introduction*, by Malcolm P. Stevens, which is incorporated by reference.

When $\alpha$ equals unity, a special condition exists in that polymer-solvent and polymer-polymer forces are balanced. Solvents that enable this condition are called θ-solvents. When temperature influences polymer solubility, the θ-temperature is the temperature at which $\alpha$ equals unity. Within the context of this invention, solvents are considered "good solvents" when $\alpha$ is about equal to 1 or more. It is appreciated that temperature influences $\alpha$, such that a good solvent may be transformed into a non-solvent merely by changing the temperature and or pressure as described herein.

In yet another embodiment of this invention, the solvent blend may contain a solvent for which the opposite is true: Polymer-polymer forces dominate polymer-solvent forces. In this case, $\alpha$ is less than one and the solvent is termed a "non-solvent," because the polymer exists in a collapsed, unexpanded state.

Within the context of this invention, it is appreciated that polymer solubility must be defined with respect to the prevailing temperature and pressure. For a given polymer, it is possible for the solvent system to contain all non-solvent at ambient conditions, which transforms into a solvent at elevated temperature/pressure (above the θ-temperature), and then reverts to a non-solvent as the temperature/pressure return to ambient conditions. Alternatively, the solvent system may comprise blends of solvents and non-solvents. In accordance with certain embodiments of the present invention, the high-energy feedstock comprises at minimum one organic material in the soluble state prior to feedstock atomization.

In a particularly useful embodiment of the invention, at least one feedstock polymer, termed the primary polymer, becomes soluble when the feedstock composition is heated and/or pressurized above ambient conditions; the polymer may or may not dissolve at ambient conditions. When a single solvent comprises the solvent system, polymer solubility may be afforded if the polymer's θ-temperature is reached, which may require heating of the feedstock composition. For example, hydroxypropylmethylcellulose (HPMC) is not soluble in ethanol at room temperature (i.e., 20° C.), but forms a true solution when heated to 50° C. Optionally, the solvent system may comprise more than one solvent, for which cosolvent effects may contribute to polymer solubility. The solvent blend may or may not dissolve the polymer at ambient conditions.

Unique powder products are produced by spray drying a high-energy feedstock, wherein the particle formation process may or may not include a non-solvent effect for the primary polymer. The non-solvent effect refers to the collapse of the primary polymer during particle formation in the particle formation chamber after feedstock atomization. The non-solvent effect may arise by two mechanisms: First, the feedstock may comprise all non-solvent (or blend of non-solvents) for the primary polymer at ambient conditions, which then became a solvent in the elevated temperature and/or pressure state, and then returned to the non-solvent state during particle formation in the particle formation chamber after atomization. Alternatively, the feedstock may comprise a solvent for the primary polymer in addition to the non-solvent. The non-solvent remains a non-solvent for the heated/pressurized feedstock, and, further remains a non-solvent during particle formation in the particle formation chamber.

In accordance with one embodiment of the invention, the primary polymer is provided with a suitable solvent/non-solvent blend (at ambient conditions) wherein the solvent possesses a lower boiling point than the non-solvent (at ambient conditions). Examples of polymer/solvent/non-solvent combinations (defined with respect to ambient conditions) include, without limitation, polyvinylpyrrolidone (PVP)/dichloromethane/acetone, polyvinylpyrrolidone-co-vinyl acetate (PVP-VA)/acetone/hexane, and ethylcellulose/acetone/water.

When the feedstock comprises a polymer/solvent/non-solvent system (at ambient conditions), polymer collapse occurs when the non-solvent concentration exceeds a critical value. This critical ratio $R_c$ can be defined:

$$R_c = \frac{\text{mass non-solvent}}{\text{mass solvent} + \text{non-solvent}}, \quad (\S 2)$$

which is the maximum fraction of the non-solvent before precipitation occurs. For practical purposes, the ratio $R_c$ can only be defined for feedstocks comprising solvent and non-solvent at ambient conditions. The ratio $R_c$ can be determined experimentally by identifying the mass fractions of each component that produce a significant increase in solution turbidity. If an $R_c$ value can be identified for a system, then the system comprises a solvent/non-solvent blend. One example is a solution consisting of about 10% (w/w) PVP, 18% (w/w) dichloromethane, and 72% (w/w) acetone, for which $R_c$ equals 0.80. Polymer systems will typically be used at solvent/non-solvent blends that are below the $R_c$ value for the system. It may be advantageous to formulate more complex polymer/solvent systems in order to control particle morphology/size as well as the crystallinity, solubility, bioavailability and/or release characteristics of the active ingredient(s).

In a highly surprising discovery, the inventors have shown that it is possible for a primary polymer to form a true solution in non-solvent-only systems at elevated temperature/pressure. Neither acetone nor toluene appreciably expand the polyvinylpyrrolidone (PVP) molecule at ambient conditions. However, it is possible to create a 1% PVP solution in an equal blend of acetone/toluene by heating and pressurizing this feedstock to 76° C. and 14 psig.

The present invention in accordance with other embodiments provides a method to increase the density of spray-dried powders. Typically, spray drying produces sphere-like particles with some degree of interior void. This void increases particle bulk without mass and creates low-density material. The non-solvent effect changes the particle size and morphology, leading to an increase in density. Particles may be smaller, wrinkled, dimpled, and/or collapsed compared to those prepared using only solvent. The solvent/non-solvent approach also reduces the mean particle size, allowing the powder to pack better. In addition, powder flow and powder-powder mixing properties are enhanced.

As noted above, the compositions prepared from a solvent/non-solvent system typically result in reduced particle size. In accordance with particular embodiments of the present invention, a composition prepared from a system spray dried from a solvent/non-solvent system as described herein results in a reduction of particle size on the order of at least about 50%, more particularly at least about 100% and in certain cases at least about 300% compared to a control composition prepared from a system comprising the same materials spray dried under similar conditions from the same solvent without the non-solvent.

In accordance with certain aspects of the present invention, small particles are provided with a relatively narrow size distribution or span. As used herein, the term "span," provides a measure of the variation in size for the active-containing particles and is calculated as follows:

$$\text{span} = \frac{d_{90} - d_{10}}{d_{50}}$$

where $d_{10}$ refers to the 10th percentile diameter by volume, $d_{50}$ refers to the 50th percentile diameter by volume, and $d_{90}$ refers to the 90th percentile diameter by volume. In accordance with particularly useful aspects of the present invention, the median particle size may be from about 0.5 μm to 100 μm, more particularly from about 1 μm to 50 μm and in certain embodiments from about 1 μm to 10 μm and the span in these embodiments may be less than about 2.0, more particularly from about 1 to 1.6, still more particularly from about 1 to 1.4 and in certain embodiments from about 1 to 1.25. Solvent/non-solvent systems are particularly suitable for producing particles falling within the above ranges.

The present invention in accordance with certain aspects provides a method to reduce or eliminate the need for secondary drying of spray-dried powders and granulated materials. These products often contain residual solvent, and it is desirable or necessary to produce a drier product. The high residual solvent content can result from formulation or processing limitations. The general practice has been to use a solvent that dissolves the solids being spray dried. In doing so, solvent can be trapped inside the spray dried powder or granulated bead due to case hardening. The intentional pairing of a lower-boiling solvent with a higher-boiling non-solvent for the materials being processed can yield products of lower residual solvent due to the effect(s) of the non-solvent on the process polymers.

In another aspect of the invention, the organic material is not polymeric. Within this context, a non-solvent is selected such that the organic material precipitates from solution during the evaporative loss of the solvent, which boils at a lower temperature than the non-solvent. Differences in organic material solubilities between the solvent and non-solvent that accomplish this precipitation during solvent evaporation are within the scope of this invention. In one embodiment, the organic material solubility is at least about 10-fold greater, more particularly at least about 25-fold greater, still more particularly at least about 50-fold greater in the solvent than in the non-solvent, and in a particularly useful embodiments of the invention, the organic material solubility is at least about 100-fold greater in the solvent than in the non-solvent. Solvent blends at the azeotropic composition can constitute a solvent or non-solvent, but together do not satisfy the criterion of solvent/non-solvent blend.

Unique particle properties can be created by the evaporative loss of solvent (comprising solvents, non-solvents, and blends thereof) from the high-energy feedstock. This evaporation occurs after feedstock atomization (or, alternatively, during the granulation processes). Atomized droplets containing a blend of solvents will experience a change in the total solvent composition due to evaporation. The method is independent of how the droplets are generated or atomized. Initially, the heated and/or pressurized feedstock presents the organic material in a soluble state. After atomization, the dispersed feedstock quickly equilibrates to the prevailing temperature and pressure in the particle formation chamber. Solvent evaporation rapidly occurs, which may or may not require additional thermal energy from a heated process gas. In accordance with certain embodiments, the process gas is maintained at or essentially at ambient conditions. In other embodiments, the non-solvent effect is manifested during the feedstock equilibration/solvent evaporation process. The non-solvent effect, described earlier, decreases the solubility of the organic molecule from its soluble state. When the organic material comprises a polymer, the polymer collapses from solution and pulls in on itself. Alternatively, when the organic material is not polymeric, the organic material precipitates due to the loss of its solubility. This loss of solvency during the particle formation process may produce highly wrinkled, dimpled, or collapsed particles that may exhibit lower residual solvent content or higher bulk or tapped density.

This non-solvent effect during particle formation may produce highly wrinkled, dimpled, or collapsed particles that may exhibit lower residual solvent content of higher density. Increased powder density is an important attribute for many applications, including pharmaceutics, health care, personal care, agriculture, biocide, and industrial chemicals. When the organic material comprises a polymer, the extent of its collapse—and therefore the net effect on the spray dried powder properties—depends on the polymer salvation factors, such as the ratio of solvent to non-solvent (if a blend is used at all), the solids concentration in the solution to be atomized, and the polymer chemical structure and molecular weight. The presence of additional polymers may contribute to the final particle morphology by their interaction with the primary polymer and the solvent system.

When the composition contains an active ingredient, the non-solvent effect may also affect the nature of the active, and thereby affect active loading, crystallinity, solubility, stability and release. Additional polymeric adjuvants may be added to serve additional purposes: further inhibit active recrystallization, further maximize active concentration, and further enhance/delay/retard dissolution rate. To accomplish these functionalities, it is necessary to suitably match the adjuvant solubilities with the solvent blend selected for the primary polymer.

The spray drying process described herein may provide several benefits over conventional spray drying operations. For example, spray dryer production rate may increase due to the high solids attainable in the closed feedstock system. Spray drying efficiency may be enhanced due to the reduced solvent content and thermal energy to the feedstock. Spray dried product may be produced without the need of heated process gas in the spray dryer. Furthermore, in accordance with certain embodiments, it may be possible to utilize solvents that are not typically used due to the enhanced solubility at increased temperature and/or pressure. As such, it may be possible to replace certain solvents with other solvents that are more preferred.

In accordance with certain embodiments of the present invention, a method is provided to reduce crystallinity and increase active concentration. Various solvent evaporation methods (e.g., rotary evaporation, spray drying) have been reported to convert crystalline actives to the amorphous form. These methods typically involve formulation of an active/polymer/solvent system. "Good solvents" are invariably selected to dissolve the active and polymer(s). In adopting this approach, however, the type and amount of polymer needed for amorphous conversion is not universal, and sometimes high polymer loading is needed to eliminate active crystallinity. The non-solvent effect profoundly and surprisingly affects the degree of activity crystallinity in a wholly different manner.

In an embodiment of the current invention, the non-solvent effect may be activated after the high-energy feedstock is atomized. Without being bound to a specific theory, it appears that the non-solvent effect alters the mechanisms of solvent evaporation and particle formulation, especially when the organic material additionally comprises a polymer. Less polymer may be needed to achieve amorphous conversion of the crystalline active. Accordingly, these compositions can contain a higher concentration of the active than can be produced using solvent-only spray drying methods. In accordance with particular embodiments of the present invention, compositions can be prepared from a system comprising a polymer and an active spray dried from a solvent/non-solvent blend that contain more than about 25% active by weight, more particularly more than about 50% active by weight and in accordance with certain embodiments more than about 75% active by weight.

Certain polymers function as solubility-enhancing polymers in that the presence of the polymer in the composition improves solubility of the active under various conditions. The solubility-enhancing polymer provides at least one of the following properties as a result of its presence in the composition compared to a control composition without the solubility-enhancing polymer or to a composition containing the crystalline form of the active:

a) an increase in initial release of at least about 25%, more particularly at least about 100% and in accordance with certain embodiments at least about 200%
b) an increase in extent of release of at least about 25%, more particularly at least about 100% and in accordance with certain embodiments at least about 200%
c) an increase in maximum plasma concentration of at least about 25%, more particularly at least about 100% and in accordance with certain embodiments at least about 200%
d) an increase in $AUC_{0\text{-}24\ h}$ of at least about 25%, more particularly at least about 100% and in accordance with certain embodiments at least about 200%.

Initial release refers to the percent of active released after 15 minutes in accordance with a standard dissolution test method. Extent of release refers to the percent of active released after 240 minutes in accordance with a standard dissolution test method.

Furthermore, compositions made by the solvent/non-solvent approach are characterized by different dissolution profiles, which may proceed at a faster rate of release or a higher extent of release, or both. In accordance with particular embodiments of the present invention, a composition prepared from a system comprising a polymer and an active spray dried under similar conditions from a solvent/non-solvent system as described herein exhibits a dissolution profile wherein the percent active released at some point in time is at least about 25%, more particularly at least about 50% and in certain cases at least about 100% greater than a control composition prepared from a system comprising the same polymer and active spray dried from the same solvent without the non-solvent. Preferably these limits are obtained within about 120 minutes, more particularly about 60 minutes and still more particularly within about 30 minutes. Dissolution profiles can be determined using test methods as described in the examples or any suitable method for the particular active in the composition.

In a further development of this invention, a polymer system is chosen so that one or more polymer(s) work with the solvent/non-solvents to create novel particle morphologies. Additional organic material(s) may be added as needed to affect the solubility and release properties of the active, as well as particle morphology. Enhanced solubility can be achieved by a number of factors, including (but not limited to): improved wettability, creation of amorphous active forms, stabilization against recrystallization, and/or co-solvation effects. In doing so, a supersaturated solution of the active is produced. "Modified release" refers to changing the time frame in which the active is released, i.e., immediate, delay, extended. These modified releases are created by matching functional polymer(s) with the appropriate solvent/non-solvent blend.

Solvents and non-solvents suitable for use in the process of the present invention can be any organic compound or water in which the organic material is soluble in the case of solvents, or insoluble, in the case of non-solvents as determined under ambient conditions. When the organic material does not comprise a polymer, the organic material solubility is about 10-fold greater in the solvent than the non-solvent, and preferably about 100-fold greater in the solvent than the non-solvent. Alternatively, when the organic material comprises one or more polymers, the choice and ratio of solvent/non-solvent depends on the primary polymer selection. Accordingly, the solvent or non-solvent selection depends on the primary polymer. Therefore, a solvent in one system may be a non-solvent in another. Particularly useful solvents and non-solvents include, but are not limited to: acetic acid, acetone, acetonitrile, anisole, 1-butanol, 2-butanol, butyl acetate, tert-butylmethyl ether, chlorobenzene, chloroform, cumene, cyclohexane, 1-2-dichloroethane, dichloromethane, 1-2-dimethoxyethane, N—N-dimethylacetamide, N—N-dimethylformamide, 1-4-dioxane, ethanol, 2-ethoxyethanol, ethyl acetate, ethylene glycol, ethyl ether, ethyl formate, formamide, formic acid, heptane, hexane, isobutyl acetate, isopropyl acetate, methanol, methyl acetate, 2-methoxyethanol, 3-methyl-1-butanol, methylbutylketone, methylcyclohexane, methylethyl ketone, methylisobutyl ketone, 2-methyl-1-propanol, N-methylpyrrolidone, nitromethane, pentane, 1-pentanol, 1-propanol, 2-propanol, propyl acetate, pyridine, sulfolane, tetrahydrofuran, tetralin, 1-2-2-trichloroethene, toluene, water, and xylene. Mixtures of solvents and mixtures of non-solvents can also be used. Azeotropes are specific ratio blends of solvents that boil at one common temperature, and are suitable for feedstock formulation.

Primary polymers and other organic materials that are suitable for use in the mixtures of the present invention should be soluble in the solvent and not soluble in the non-solvent. Specific examples of useful organic materials include, but are not limited to: aliphatic polyesters (e.g., poly D-lactide), sugar alcohols (e.g., sorbitol, maltitol, isomalt), carboxyalkylcelluloses (e.g., carboxymethylcellulose and crosslinked carboxymethylcellulose), alkylcelluloses (e.g., ethylcellulose), gelatins, hydroxyalkylcelluloses (e.g., hydroxymethylcellulose, hydroxypropylcellulose (HPC)), hydroxyalkylalkylcelluloses (e.g., hydroxypropylmethyl cellulose (HPMC)), hydroxyalkylalkylcellulose derivatives (e.g. hydroxypropylmethyl cellulose acetate succinate, hydroxypropylmethyl cellulose phthalate) polyamines (e.g., chitosan), polyethylene glycols (e.g., PEG 8000, PEG 20000), methacrylic acid polymers and copolymers (e.g., Eudragit® series of polymers of Rohm Pharma GmbH), homo- and copolymers of N-vinyl pyrrolidone (e.g., polyvinylpyrrolidone, crosslinked polyvinylpyrrolidone and polyvinylpyrrolidone-co-vinyl acetate), homo- and copolymers of vinyllactam, starches (e.g. cornstarch, sodium starch glycolate), polysaccharides (e.g., alginic acid), poly glycols (e.g., polypropylene glycol, polyethylene glycol), polyvinyl esters (e.g., polyvinyl acetate), refined/modified shellac. The amount of the polymer or organic material present in the mixture may range from about 1% to about 95%, more particularly from about 5% to 90%, by weight of the mixture. Blends of organic materials may also be used.

The feedstock composition may also include an active material. Although the following description is primarily directed to pharmaceutically active materials, the present invention is not limited to pharmaceutically active materials. The scope of the present invention also includes active ingredients used in the personal care (e.g., hair care, skin care or oral care), agriculture, biocide and other industrial or consumer applications. As used herein "pharmaceutically active materials" is intended to include nutritionally active materials, dietary supplements, and vitamin materials. The mixture may contain from about 1% to about 95% active, more particularly from about 20% to about 80% active, depending on the desired dose of the active. Actives that can be used in accordance with the present invention are not particularly limited. Examples of actives that may be used include, but are not limited to: abacavir sulfate, acebutolol, acetaminophen, acemetacin acetylcysteine, acetylsalicylic acid, acyclovir, adefovir dipivoxil, alprazolam, albumin, alfacalcidol, allantoin, allopurinol, ambroxol, amikacin, amiloride, aminoacetic acid, amiodarone, amitriptyline, amlodipine, amoxicillin, amoxicillin trihydrate, amiodarone hydrochloride, amphotericin B, ampicillin amprenavir, aprepitant, anastrozole, ascorbic acid, aspartame, astemizole, atazanavir sulfate, atenolol, atorvastatin calcium, azathioprine, azithromycin, azithromycin dihydride, beclomethasone, benserazide, benzalkonium hydroxide, benzocaine, benzoic acid, betametasone, bezafibrate, bicalutamide, biotin, biperiden, bisoprolol, bosentan, bromazepam, bromhexine, bromocriptine, budesonide, bufexamac, buflomedil, buspirone, caffeine, camphor, candesartan cilexetil, captopril, carbamazepine, carbidopa, carboplatin, carvedilol, cefachlor, cefalexin, cefadroxil, cefazolin, cefdinir, cefixime, cefotaxime, ceftazidime, ceftriaxone, cefuroxime, celecoxib, chloramphenicol, chlorhexidine, chlorpheniramine, chlortalidone, choline, cilastatin, cilostazol, cimetidine, ciprofloxacin, cisapride, cisplatin, citalopram hydrobromide, clarithromycin, clavulanic acid, clomipramine, clonazepam, clonidine, clopidogrel bisulfate, clotrimazole, clozapine, codeine, colestyramine, coenzyme Q10, cromoglycic acid, cyanocobalamin, cyclosporin, cyproterone, danazole, delavirdine mesylate, desipramine, desloratadine, desmopressin, desogestrel, dexamethasone, dexpanthenol, dextromethorphan, dextropropoxiphene, diazepam, diclofenac, digoxin, dihydrocodeine, dihydroergotamine, diltiazem, diphenhydramine, dipyridamole, dipyrone, disopyramide, docetaxel, domperidone, dopamine, doxycycline, doxorubicin hydrochloride, dronabinol, dutasteride, efavirenz, eletriptan hydrobromide, emtricitabine, enalapril, enrofloxacin, entacapone, ephedrine, epinephrine, eplerenone, eprosartan mesylate, ergocalciferol, ergoloid mesylate, ergotamine tartrate, erythromycin, escitalopram oxalate, estradiol, ethinylestradiol, etoposide, exemestane, ezetimibe, famotidine, felodipine, fenofibrate, fenoterol, fentanyl, fexofenadine hydrochloride, finasteride, flavin mononucleotide, fluconazole, flunarizine, fluorouracil, fluoxetine, flurbiprofen, fluphenazine hydrochloride, flutamide, fluticasone propionate, fluvastatin, fosamprenavir, fosamprenavir calcium, furosemide, gabapentin, galantamine hydrobromide, ganciclovir, gemfibrozil, gentamicin, ginkgo biloba, glibenclamide, glimepiride, glipizide, Glycyrrhiza Glabra, glyburide, guaifenesin, guanabenz, haloperidol, heparin, hyaluronic acid, hydrochlorothiazide, hydrocodone, hydrocortisone, hydromorphone, hydroxytetracycline, ipratropium hydroxide, ibuprofen, idarubicin, imipenem, imipramine hydrochloride, indinavir sulfate, indomethacin, iohexyl, iopamidol, irinotecan, isosorbide dinitrate, irbesartan, isosorbide mononitrate, isotretinoin, isradipine, itraconazole, ketotifen, ketoconazole, ketoprofen, ketorolac, labetalol, lactulose, lamivudine, lamotrigine, lansoprazole, lecithin, levetiracetam, levocamitine, levodopa, levoglutamide, levonorgestrel, levothyroxine, lidocaine, lipase, lisinopril, loperamide, lopinavir, loratadine, lorazepam, lovastatin, medroxyprogesterone, meloxicam, melphalan, menthol, mercaptopurine, mesalamine, methotrexate methyldopa, N-methylephedrine, methylprednisolone, metoclopramide, metolazone, metoprolol, miconazole, midazolam, minocycline, minoxidil, misoprostol, mitotane, modafanil, mometasone, morphine, mosapride, multivitamins and minerals, nabumetone, nadolol, naftidrofuryl, naproxen, nefazodone, nelfinavir mesylate, neomycin, nevirapine, nicardipine hydrochloride, nicergoline, nicotinamide, nicotine, nicotinic acid, nifedipine, nimodipine, nisoldipine, nitrendipine, nizatidine, norethisterone, norfloxacin, norgestrel, nortriptyline, nystatin, ofloxacin, olanzepine, olmesartan medoxomil, omeprazole, ondansetron, orlistat, oxcarbazepine, paclitaxel, pancreatin, panthenol, pantoprazole, pantothenic acid, paracetamol, paroxetine hydrochloride, penicillin G, penicillin V, perphenazine, phenobarbital, phenylephrine, phenylpropanolamine, phenyloin, pimecrolimus, pimozide, pioglitazone hydrochloride, piroxicam, polymyxin B, povidone-iodine, pravastatin sodium, prazepam, prazosin, prednisolone, prednisone, proglumetacin, propafenone hydrochloride, propranolol, propofol, pseudoephedrine, pyridoxine, quinaprile hydrochloride, quinidine, raloxifine hydrochloride, ramipril, ranitidine, reserpine, resveratrol, resveratrol-analogues, retinol, ribavirin, riboflavin, rifampicin, risperidone, ritonavir, rosuvastatin calcium, rutoside, saccharin, salbutamol, salcatonin, salicylic acid, salmetrol xinafoate, saquinavir, sertaline, sildenafil citrate, simvastatin, sirolimus, somatropin, sotalol, spironolactone, stavudine, sucralfate, sulbactam, sulfamethoxazole, sulphasalazine, sulpiride, tacrolimus, tadalafil, tamoxifen, tamsulosin hydrochloride, tegafur, tenofovir disoproxil fumarate, tenoxicam, teprenone, terazosin, terbinafine hydrochloride, tegaserod maleate, telmisartan, terbutaline, terfenadine, thalidomide, theophylline, thiamine, tiaprofenic acid, ticlopidine, timolol, tizanidine hydrochloride, topiramate, trandolapril, tranexamic acid, tretinoin, triamcinolone acetonide, triamterene, triazolam, trimethoprim, troxerutin, uracil, valdecoxib, valgancyclovir hydrochloride, valproic acid, valrubicin, valsartan, vancomycin, verapamil, vardenafil hydrochloride, vitamin E, zafirlukast, zalcitabine, zalephon, zidovudine, ziprasidone, zolpidem tartrate, zonisamide, or zotepine.

The feedstock composition may also contain additional organic materials that can modify properties of the final product. For example, certain organic substances can be included to control particle morphology/size as well as the solubility, bioavailability and release characteristics of the active ingredient. Additional organic material may also be included in the mixture to further inhibit active recrystallization, further maximize active concentration and further enhance/delay/retard dissolution rate. Additional organic materials that can be incorporated into this system are not particularly limited. In one embodiment of this invention the additional organic material is polymeric.

Feedstock compositions typically contain from about 40% to 99.9% by weight total solvent (including non-solvent), more particularly from about 80% to 95% by weight total solvent based on the total weight of the mixture. If the feedstock comprises a polymer/solvent/non-solvent (defined at ambient conditions), then the critical ratio $R_c$ can vary from about 0.01-0.99, more particularly from about 0.1-0.9, still more particularly from about 0.3-0.8.

In addition to the solvent, polymer and any active, the formulation may also include other ingredients to improve performance, handling or processing of the mixture. Typical ingredients include, but are not limited to, surfactants, pH modifiers, fillers, complexing agents, solubilizers, pigments, lubricants, glidants, flavor agents, plasticizers, taste masking agents, disintegrants, disintegrant aids (e.g., calcium silicates), etc. Examples of useful surfactants include, but are not limited to, sodium lauryl sulfate, docusate sodium, sorbitan monooleate, and sorbitan trioleate. Examples of useful fillers include, but are not limited to, lactoses, dextrin, sugars, sugar alcohols, and silica. These excipients may be used for customary purposes and in typical amounts.

The equipment used in the process of the present invention can take the form of any apparatus that accomplishes the formation of powder and granulated products from a high-energy feedstock. Such equipment includes spray dryers of any commercially viable design. Examples of specific spray-drying devices include spray dryers manufactured by Niro, Inc. (e.g., SD-Micro®, PSD®-1, PSD®-2, etc.), the Mini Spray Dryer (Buchi Labortechnik AG), spray dryers manufactured by Spray Drying Systems, Inc. (e.g., models 30, 48, 72), and SSP Pvt. Ltd. Per an embodiment of the invention, a heated process gas is not required, and in fact, a cooled process gas may be required to form solid-phase powders.

Spray-drying processes and spray-drying equipment are described generally in Perry's Chemical Engineers' Handbook, Sixth Edition (R. H. Perry, D. W. Green, J. O. Maloney, eds.) McGraw-Hill Book Co. 1984, pages 20-54 to 20-57. More details on spray-drying processes and equipment are reviewed by Marshall "Atomization and Spray-Drying," 50 Chem. Eng. Prog. Monogr. Series 2 (1954). The contents of these references are hereby incorporated by reference.

The term "spray-drying" is used conventionally and, in general, refers to processes involving breaking up liquid mixtures into small droplets and rapidly removing solvent from the mixture in a container (spray-drying apparatus) where there is a strong driving force for solvent evaporation from the droplets. Atomization techniques include two-fluid and pressure nozzles, and rotary atomizers. The strong driving force for solvent evaporation is generally provided by maintaining the partial pressure of solvent in the spray-drying apparatus well below the vapor pressure of the solvent at the temperatures of the drying droplets. This may be accomplished by either (1) maintaining the pressure in the spray-drying apparatus at a partial vacuum; (2) mixing the liquid droplets with a warm drying gas; or (3) both.

Generally, the temperature and flow rate of the drying gas and the design of the spray dryer are chosen so that the atomized droplets are dry enough by the time they reach the wall of the apparatus that they are essentially solid and so that they form a fine powder and do not stick to the apparatus wall. The actual length of time to achieve this level of dryness depends on the size of the droplets, the formulation, and spray dryer operation. Following the solidification, the solid powder may stay in the spray-drying chamber for 5-60 seconds, further evaporating solvent from the solid powder. The final solvent content of the particle as it exits the dryer should be low, since this improves the handling and stability of the product. Generally, the residual solvent content of the spray-dried composition should be less than about 10% by weight and preferably less than about 2% by weight. Although not typically required in accordance with the present invention, because the presence of a non-solvent produces a spray-dried powder of lower residual solvent content, it may be useful in accordance with certain embodiments of the present invention to subject the spray-dried composition to further drying to lower the residual solvent to even lower levels. Additional detail with respect to a particular spray-drying process is described in more detail in the examples. However, the operating conditions to spray dry a powder are well known in the art and can be easily adjusted by the skilled artisan. Furthermore, the examples describe results obtained with a laboratory scale spray dryer. One of ordinary skill in the art would readily appreciate the variables that must be modified to obtain similar results with a production scale unit.

The feedstock also can be distributed as a cast film with or without a substrate carrier. The carrier may comprise porous or non-porous substrates, including, but not limited to, granules, powders, tablets, or sheets. Alternatively, the feedstock may be distributed as a film without a substrate carrier, and the feedstock solvents removed through evaporation to produce a solid or solid-like material.

Compositions of the invention may be presented in numerous forms commonly used in a wide variety of industries. Exemplary presentation forms are powders, granules, and multiparticulates. These forms may be used directly or further processed to produce tablets, capsules, or pills, or reconstituted by addition of water or other liquids to form a paste, slurry, suspension or solution. Various additives may be mixed, ground, or granulated with the compositions of this invention to form a material suitable for the above product forms.

Compositions of the invention may be formulated in various forms so that they are delivered as a suspension of particles in a liquid vehicle. Such suspensions may be formulated as a liquid or as a paste at the time of manufacture, or they may be formulated as a dry powder with a liquid, typically water, added at a later time but prior to use. Such powders that are constituted into a suspension are often referred to as sachets or oral powders for constitution (OPC). Such product forms can be formulated and reconstituted via any known procedure.

In pharmaceutical applications, compositions of the present invention may be delivered by a wide variety of routes, including, but not limited to, oral, nasal, rectal, vaginal, subcutaneous, intravenous, and pulmonary. Generally, the oral route is preferred.

Oral, solid-dose pharmaceutical spray dried powders typically have a mean particle size of about 0.5 µm-500 µm and are generally prepared from solutions at concentrations of 1% or more total solids, more particularly from about 2-50%, and still more particularly from about 3-25% solids.

Oral, solid dose pharmaceutical granules typically have a mean particle size of about 50 µm-5000 µm. Techniques to produce granules include, but are not limited to, wet granulation and various fluid bed granulating methods.

Compositions produced in accordance with some embodiments of the invention are present in solid state forms such as solid solutions or solid dispersions. The compositions may be primarily or essentially all in such forms or contain certain components in such form. These forms can provide benefits such as improved bioavailability, solubility, etc.

The present invention is described in more detail by the following non-limiting examples.

EXAMPLES

Example 1

A. A dispersion was made containing 1 efavirenz (EFV): 3 polyvinylpyrrolidone (PVP) and 2% sodium lauryl sulfate (SLS) in 10% dichloromethane, 90% acetone at 10% total solids. A true solution was not created with this amount of acetone, which is a non-solvent for PVP under ambient conditions.

B. The dispersion was placed into a pressure vessel (Parr Instrument Co.) and heated to 80° C. and 25 psig. Under these conditions the PVP dissolved, yielding a clear, true solution.

C. The heated solution was evacuated to a spray dryer (SD-Micro®, Niro Inc.) operating with a two-fluid nozzle. The process gas was heated to an inlet temperature of 65° C.

D. A powder collected in the cyclone jar and had a total residual solvent content of 3.2%.

Figure 2:
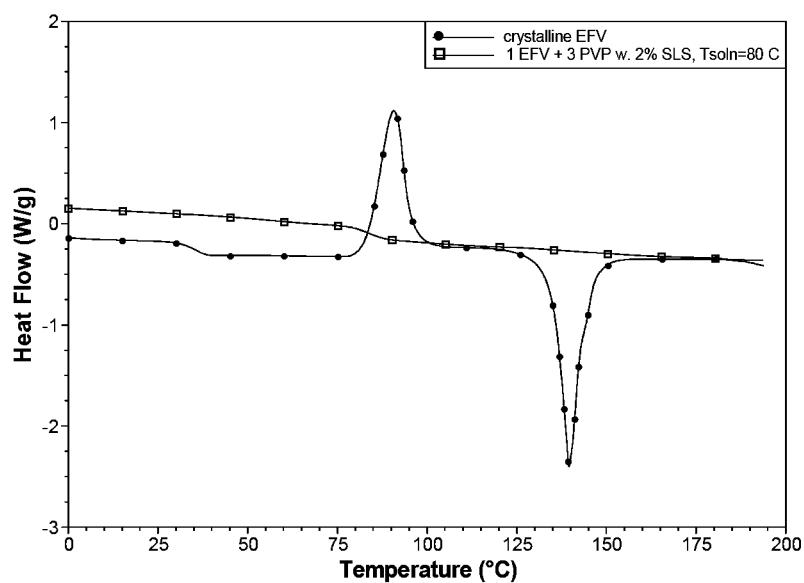
FIG. 2 is a plot of heat flow versus temperature for the particles produced in accordance with Example #1.

E. Analysis of efavirenz crystallinity by DSC (Q1000®, TA Instruments) showed the complete absence of an efavirenz melt endotherm at about 139° C. The spray dried powder contained only completely amorphous efavirenz (FIG. 2).

Figure 3A:
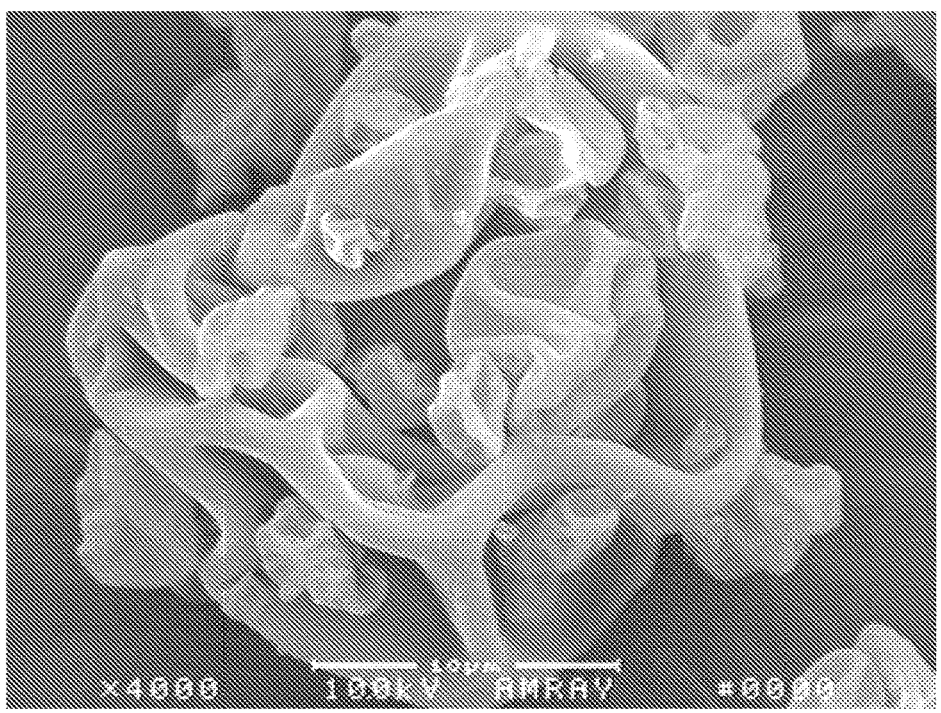
FIGS. 3A-B are photomicrograph images of particles produced in accordance with Example #1.
Figure 3B:
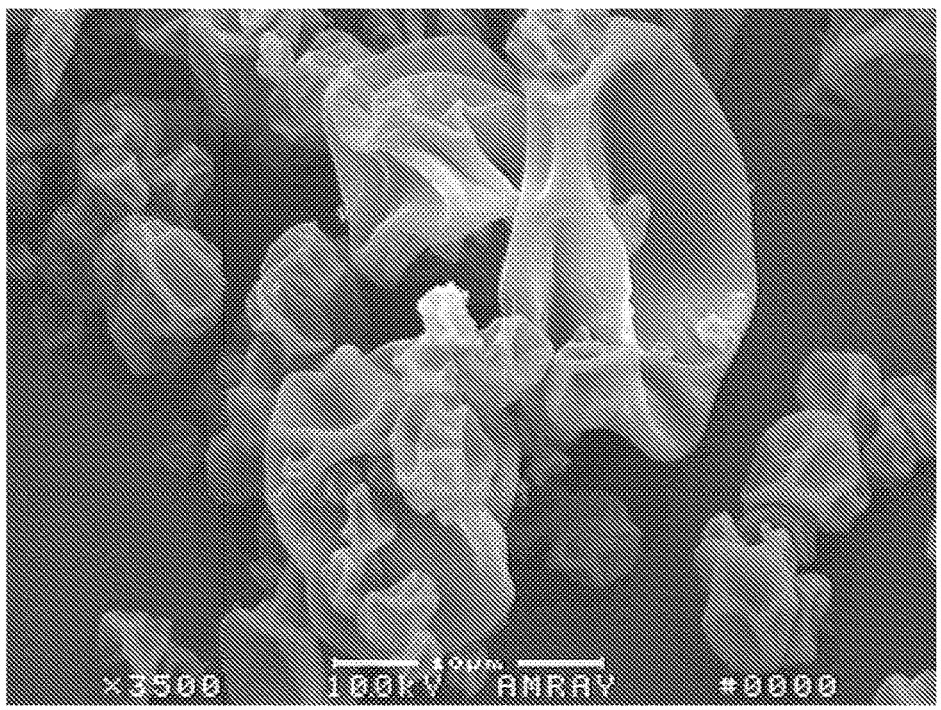

F. Based on scanning electron microscopy, the powder produced by this formulation and method had a particle size of about less than 10 µm (FIGS. 3A and 3B). Particles are substantially collapsed with extensive folds such that the particles are not spheres.

Example 2

A. A second powder was produced using the method described in Example 1, except the dispersion was heated to 105° C. at 50 psig to produce a clear, true solution.

B. A powder collected in the cyclone jar and had a total residual solvent content of 6.2%.

Figure 4:
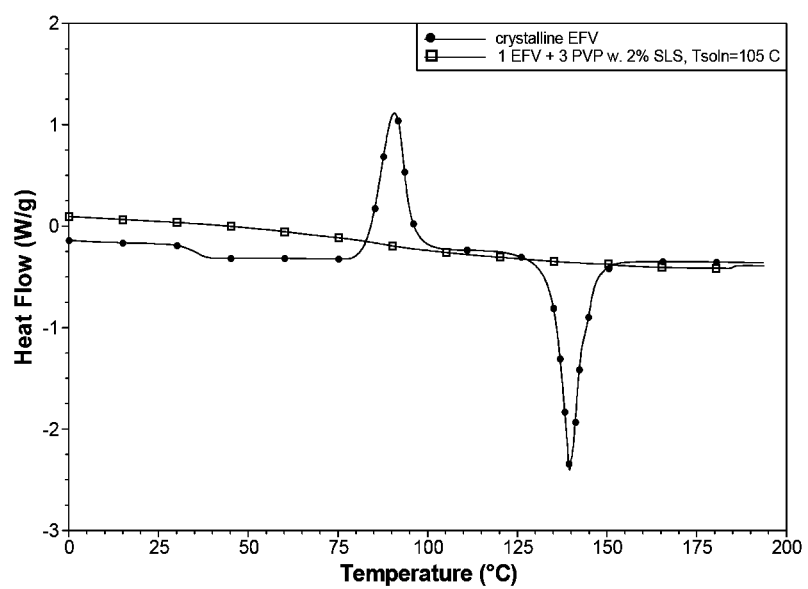
FIG. 4 is a plot of heat flow versus temperature for compositions produced in accordance with Example #2.

C. Analysis of efavirenz crystallinity by DSC (Q1000®, TA Instruments) showed the complete absence of an efavirenz melt endotherm at about 139° C. The spray dried powder contained only completely amorphous efavirenz (FIG. 4).

Figure 5A:
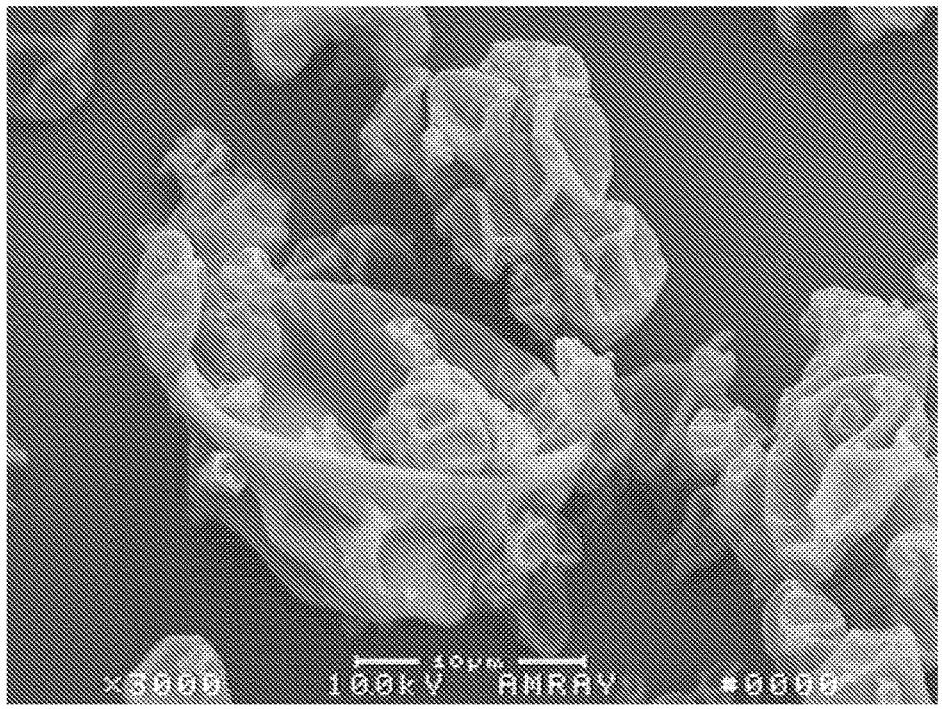
FIGS. 5A-B are photomicrograph images of particles produced in accordance with Example #2.
Figure 5B:
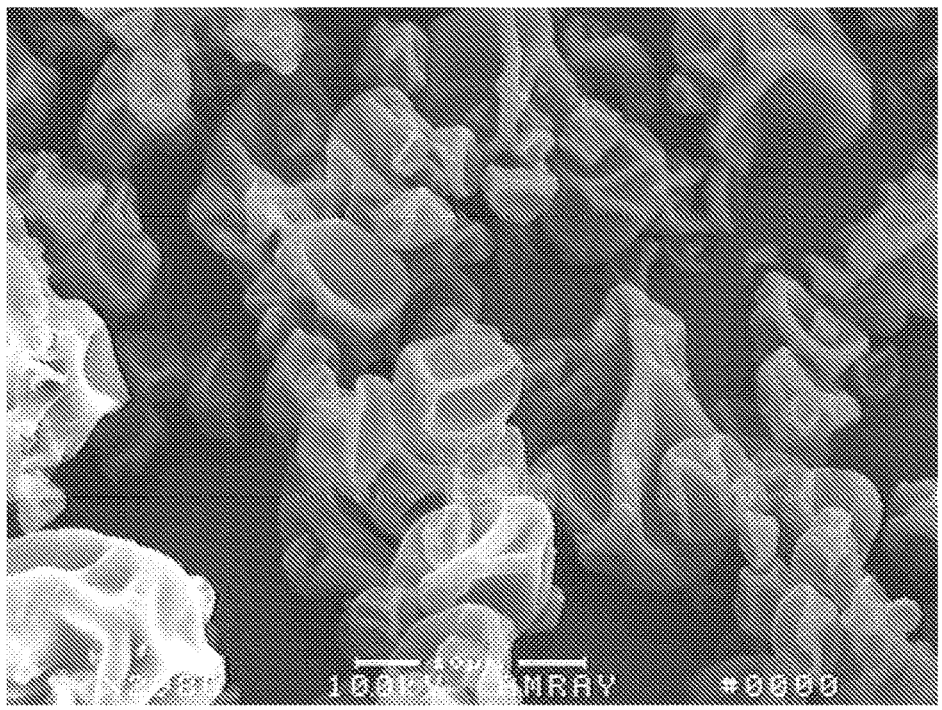

D. Based on scanning electron microscopy, the powder produced by this formulation and method had a particle size of about less than 10 µm (FIGS. 5A and 5B). Particles are substantially collapsed with extensive folds such that the particles are not spheres.

Example 3

A. The dissolution properties of both amorphous compositions were tested and compared to crystalline EFV. An amount equivalent to 50 mg efavirenz was analyzed. Powders were hand-filled into size 1 hard gelatin capsules (Shinogi Qualicaps) with an additional 15% croscarmellose sodium (Ac-Di-Sol®, FMC BioPolymers). USP apparatus II (paddles) (VK 7010®, Varian Inc.) was used, with a bath temperature of 37° C. and a paddle speed of 50 rpm for 60 minutes.

Figure 6:
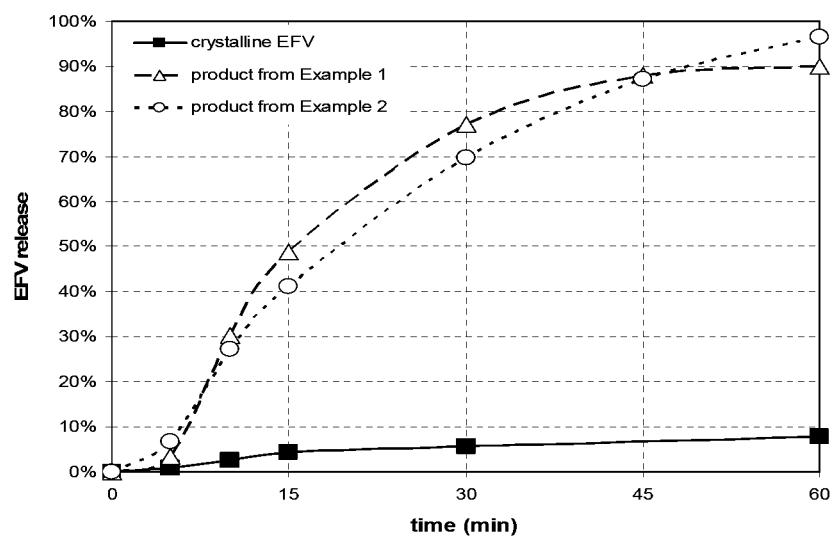
FIG. 6 is a plot of percent release versus time for compositions produced in accordance with Examples #1 and #2 compared to crystalline efavirenz.

B. Each of the amorphous powders from Examples 1 and 2 achieved higher rate of release and maximum aqueous concentration than the crystalline form (FIG. 6, Table 2).

The initial rate of release from the amorphous powders was more than 10-times higher than the crystalline form. The amorphous product spray dried from a solution temperature of 105° C. yielded essentially complete release of this poorly water-soluble drug.

TABLE 2

A comparison of dissolution properties for Example 3.

| composition | rate of release, 0-15 min (mg/min) | extent of release |
|---|---|---|
| crystalline EFV | 0.13 | 10% |
| this invention, $T_{soln}$ = 80° C. | 1.6 | 90% |
| this invention, $T_{soln}$ = 105° C. | 1.4 | 97% |

Example 4

A dispersion was prepared containing 1 ezetimibe: 1 PVP K-12 at 1% total solids in ethyl acetate at standard laboratory conditions (about 25° C. and 1 atmosphere). Under these conditions, ezetimibe (EZE) is soluble in ethyl acetate, which is a non-solvent for PVP, meaning that the polymer molecule does not expand ($\alpha<1$).

The dispersion was placed in the pressure vessel of Example 1, and was heated to 110° C. at 45 bar. A true, clear solution was created under these conditions.

The heated and pressurized solution was evacuated to a spray dryer (Mobile Minor, Niro Inc.), equipped with a 0.5 mm two-fluid nozzle. The spray dryer inlet temperature was 110° C., the outlet temperature was 45° C., and the atomization pressure was 1.0 bar. A powder product was collected in the spray dryer's cyclone collection jar.

The assay of the ezetimibe cyclone product was measured using an HPLC method based on work by Sistla et al., "Development and validation of a reverse-phase HPLC method for the determination of ezetimibe in pharmaceutical dosage forms," *J. Pharma Bio Anal*, 39 (2005), 517-522. An Alliance 2695 HPLC system was used with a 2996 photo-diode array detector (Waters Corp.). A 250 mm×4.6 mm Phenomenex C18 Luna column was used, and the mobile phase was 60% acetonitrile:40% water with a flow rate of 1.5 mL/min. The assay was measured to be 84% ezetimibe, which was not corrected for water or residual ethyl acetate content.

Figure 7:
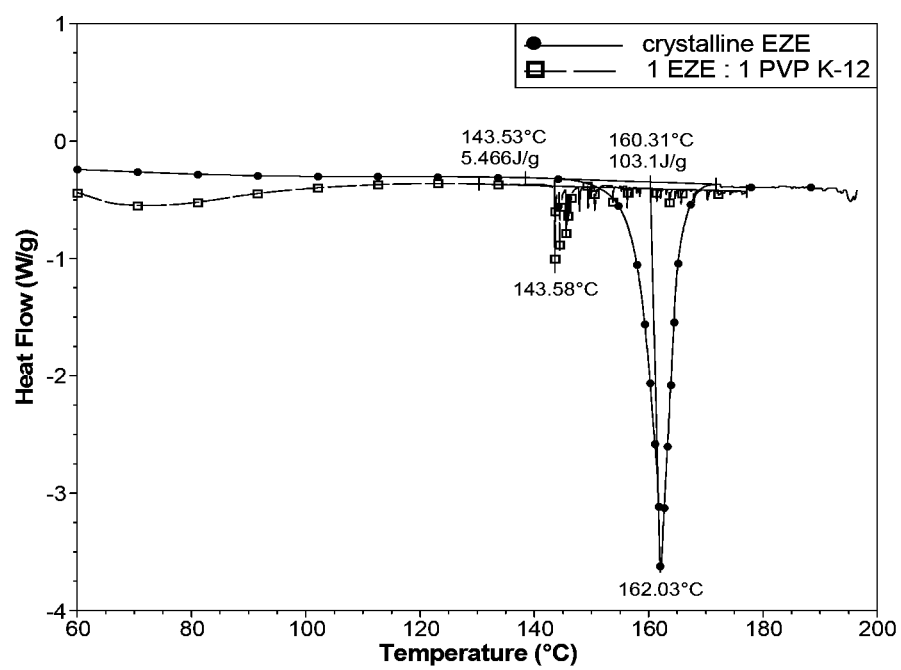
FIG. 7 is a plot of heat flow versus temperature for the particles produced in accordance with Example #4.

The thermal properties of the ezetimibe composition were measured using differential scanning calorimetry (Q1000, TA Instruments). A heating rate of 10° C./min was used with crimped, aluminum pans. The melting enthalpy of the high pressure, high temperature product (11 J/g, formulation corrected) was considerably less than the crystalline form of the drug (103 J/g) (See FIG. 7).

Changes may be made by persons skilled in the art in the compositions and/or in the steps or the sequence of steps of the method of manufacture described herein without departing from the spirit and scope of the invention as defined in the following claims.

What is claimed is:

1. A spray drying method for preparing powders having a particle size of about less than 10 μm and with increased density comprising:
   a) providing a feedstock comprising an organic material in a solvent system comprising a non-solvent, wherein:
      the organic material comprises polyvinylpyrrolidine,
      the non-solvent comprises a non-solvent for polyvinylpyrrolidine under ambient conditions,
      the solvent system functions as a non-solvent for the polyvinylpyrrolidine under ambient conditions, and
      the feedstock is at an elevated temperature of about 40° C. to about 200° C. and an elevated pressure of greater than 1 atmosphere (gauge) to about 20 atmospheres (gauge) such that the solvent system functions as a solvent for the polyvinylpyrrolidine;
   b) delivering the feedstock to a device capable of atomizing the feedstock into droplets; and
   c) evaporating the solvent system from the droplets of the feedstock, thereby forming particles of the organic material.

2. The method of claim 1 wherein the organic material further comprises a pharmaceutically active material.

3. The method of claim 2 wherein the organic material further comprises a polymer other than polyvinyl pyrrolidine.

4. The method of claim 3 wherein the feedstock further comprises one or more pharmaceutically acceptable ingredients.

5. The method of claim 1 wherein the solvent system comprises a solvent and non-solvent pair for at least one organic material present at a ratio of from about 5% solvent: 95% non-solvent to about 95% solvent:5% non-solvent.

6. The method of claim 1 wherein the concentration of the organic material in the feedstock is from about 1% to about 90% by weight.

7. The method of claim 1 wherein the feedstock further comprises a second organic material.

8. The method of claim 7 wherein the second organic material is a pharmaceutically active agent.

9. The method of claim 2 wherein the pharmaceutically active material exhibits an increased rate of release compared to a control composition prepared using a solvent system without a non-solvent.

10. The method of claim 2 wherein the pharmaceutically active material exhibits an increased extent of release compared to a control composition prepared using a solvent system without a non-solvent.

11. The method of claim 8 wherein the solvent system comprises a solvent and a non-solvent for the polymer.

12. The method of claim 11 wherein steps b) and c) comprise spray drying the feedstock to form a spray-dried composition.

13. The method of claim 12 wherein said spray dried composition comprises at least about 25% by weight pharmaceutically active material.

14. The method of claim 12 wherein said spray dried composition comprises at least about 75% by weight pharmaceutically active material.

15. The method of claim 12 wherein said spray dried composition exhibits a dissolution profile wherein the percent active released is at least about 25% greater than a control composition prepared from a system comprising the same polymer and active spray dried from the same solvent without the non-solvent.

16. The method of claim 12 wherein said spray dried composition exhibits a dissolution profile wherein the initial rate of active released is at least about 25% greater than a control composition prepared from a system comprising the same polymer and active spray dried from the same solvent without the non-solvent.

17. The method of claim 12 wherein said spray dried composition exhibits a dissolution profile wherein the percent active released is at least about 100% greater than a control composition prepared from a system comprising the same polymer and active spray dried from the same solvent without the non-solvent.

18. The method of claim 1 wherein the solvent system consists of a non-solvent.

19. The method of claim 18 wherein the non-solvent is selected from the group consisting of acetone, toluene, ethyl acetate, and mixtures thereof.

* * * * *